United States Patent [19]

Grylls et al.

[11] 4,188,407
[45] * Feb. 12, 1980

[54] PROCESSES FOR PRODUCING ACTIVE DRIED YEAST

[75] Inventors: Frederick S. M. Grylls, Morden, England; Stanley D. Rennie, Menstrie; Michael Kelly, Stirling, both of Scotland

[73] Assignee: The Distillers Company (Yeast) Limited, Morden

[ * ] Notice: The portion of the term of this patent subsequent to Mar. 28, 1995, has been disclaimed.

[21] Appl. No.: 892,802

[22] Filed: Apr. 3, 1978

Related U.S. Application Data

[63] Continuation-in-part of Ser. No. 716,852, Aug. 23, 1976, abandoned.

[51] Int. Cl.² ............................................. C12C 11/30
[52] U.S. Cl. ........................................ 426/62; 34/10; 426/473
[58] Field of Search ................. 426/60, 61, 62, 473, 426/465, 285, 453, 519, 467, 470, 456; 195/74, 97, 98, 143; 34/10, 12, 59, 60

[56] References Cited

U.S. PATENT DOCUMENTS

| 235,116 | 12/1880 | Alden | 426/467 X |
|---|---|---|---|
| 2,513,369 | 7/1950 | Shaw | 34/10 |
| 2,749,625 | 6/1956 | Clairmonte | 34/60 X |
| 2,921,854 | 1/1960 | Parker | 426/453 X |
| 3,885,049 | 5/1975 | Taylor | 426/473 X |
| 3,962,467 | 6/1976 | Burrows | 426/465 X |
| 4,046,921 | 9/1977 | Akao et al. | 195/143 X |
| 4,081,558 | 3/1978 | Grylls et al. | 426/473 X |

FOREIGN PATENT DOCUMENTS

| 544638 | 8/1957 | Canada | 426/467 |
|---|---|---|---|
| 937461 | 9/1963 | United Kingdom | 426/467 |

*Primary Examiner*—Kenneth M. Schor
*Attorney, Agent, or Firm*—Lawrence Rosen; E. Janet Berry

[57] ABSTRACT

A process is described of making active dried yeast comprising drying moist yeast particles in a fluidized bed and, during the fluidized bed drying, and before the yeast has a dry matter content of 80%, subjecting the particles to disintegration forces while they are fluidized, the disintegration forces being sufficient to prevent any substantial increase in particle size but insufficient to break the yeast cells themselves.

7 Claims, 1 Drawing Figure

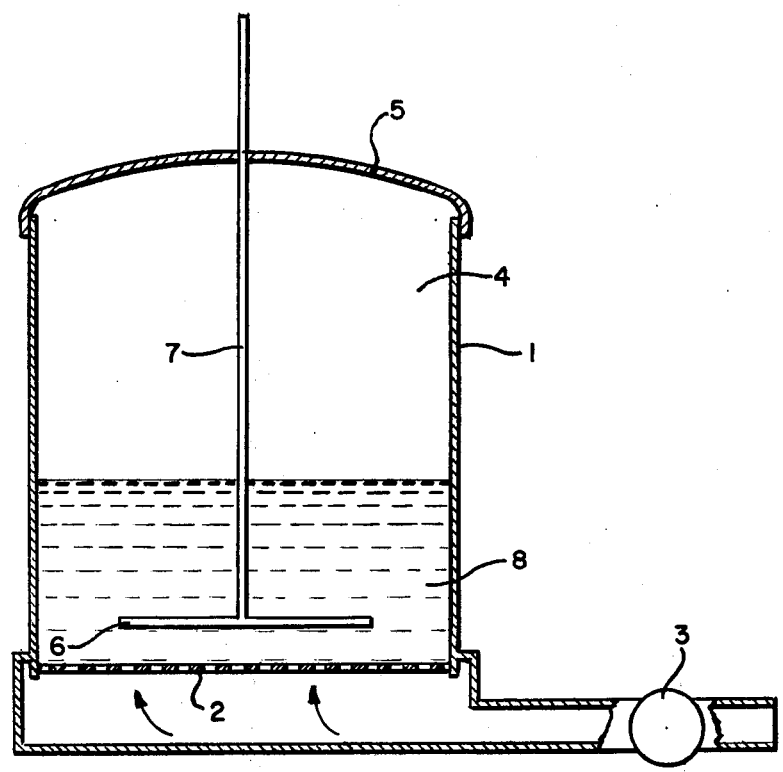

PROCESSES FOR PRODUCING ACTIVE DRIED YEAST

This application is a continuation-in-part of our application Ser. No. 716,852 filed Aug. 23, 1976, now abandoned.

Active dried yeast is well known and is made by drying particles of moist yeast until the dry matter content is, for example, from 90 to 97%. It is well known that the drying conditions significantly affect the final activity of the yeast. Traditionally active dried yeast has generally been made by drum drying, as a result of which the product is in the form of pellets, and these have a rather hard surface structure and a substantial proportion of them are rather large, for example having a minimum dimension of 1, or more usually, 2mm or more. More recently processes for making active dried yeast in powder form have been known. In these the yeast particles are smaller than in pellet yeast, for example generally having a minimum dimension of less than 1 mm, and are not so hard as in pellet yeast. Generally the methods involve forming small moist particles and the drying yhese by one of the various methods, a preferred method being fluidised bed drying. We use this term to encompass any method in which the particles are held in a bed and are at least partially entrained in the drying gas.

One particularly satisfactory method of making active dried yeast is described in our British Patent Specification No. 1,369,551. In this crumbly yeast is fed continuously into a mill through which air is passed, the yeast is disintegrated in the mill to a powder, the powder is continuously carried out of the mill in a stream of air, and is then dried in, for instance a fluidised bed, the drying being conducted in the substantial absence of any force tending to compress the powder, at least until the dry matter content exceeds 75% by weight. In an earlier method, described in our British Patent Specification No. 1,140,016, it is stated the drying is conducted without any mechanical mixing or the application of pressure on the yeast.

When a fluidised bed drying method is used a product comprising extremely satisfactory active dried yeast is obtained. However when the product that is subjected to drying is of very uniform small particle size a significant proportion, often at least 10% and sometimes as much as 40 or 50% by weight, of the particles after drying have a particle size greater than is desired. For example the initial moist particles and therefore desirably the final dry particles should all have the size of less than 0.35 mm and yet sieving of the dried product with a 0.35 mm sieve may hold back from 10 to 50% of the dried product. Whilst this sieving can be conducted in such a way as to break down some of the particles, or they can be broken down by further milling, this is not entirely satisfactory as the resultant particles generally have less activity than the remainder.

It is well known that while yeast is being dried it passes through the so-called "sticky stage" during which it has a very high tendency to agglomerate to itself. This sticky stage occurs at dry matter contents between about 50 and about 70 or 80%. Because of the sensitivity and high tendency of yeast particles to agglomerate as they pass through this stage, it is known that great care has to be exercised in handling them at this stage.

The present stage of knowledge, therefore, is that the described and other fluidised bed methods of making powdered active dried yeast are capable of being operated to produce satisfactory active dried yeast but suffer from the disadvantage that they produce a substantial proportion of over-size particles that are best rejected, and that great care must be exercised in handling the yeast while it passes through the sticky stage.

Our object has been to minimise the proportion of oversize particles, and preferably to eliminate it absolutely, without having any substantial adverse effect on the activity of the remainder of the yeast particles.

According to the present invention powdered active dried yeast having a dry matter content of 90 to 97% by weight is made by a process comprising drying moist yeast particles less than 0.35 mm in size in a fluidised bed and subjecting the yeast particles in the fluidised bed to forces capable of disintegrating agglomerates of yeast particles, the said forces being applied continuously or intermittently throughout at least most of the time that the dry matter content of the yeast is between 50 and 70% and being sufficient to prevent any substantial increase in particle size but insufficient to break the yeast cells themselves whereby an increased proportion of the dried particles are less than 0.35 mm in size. Whereas, without the application of disintegration forces, a significant proportion of particles are over 0.35 mm in the invention substantially all the dried particles are less than 0.35 mm in size. Thus less are over-size than in the prior method and generally the proportion of particles above 0.35 mm in size is below 20%, and often less tha 10%.

The moist yeast particles may be made by comminution of compressed yeast, for instance by a milling method such as is described in British Patent Specifications Nos. 1,140,016 or more preferably, 1,369,551 as described above. Other comminution methods that may be used include extrusion through orifices of appropriate size, for instance as described in British Patent Specification No. 1,230,205. The compressed yeast, and the moist particles at the start of the fluidised bed drying, generally have a dry matter content such that the yeast is in a crumbly state, for example 27 to 40%, preferably 30 to 40%.

Another method of making the moist particles is by spray drying a yeast suspension, for example a cream having a dry matter content of below 25%, and generally below 20%. By appropriately controlling the spray drying conditions moist particles having a dry matter content of from 40 to 50%, for instance from 40 to 45%, may be obtained. Such a method is described in our British Patent Specification No. 1,196,786.

Reference should be made by these four patent specifications for full description of suitable apparatus and methods.

It is essential in the invention that the particles are subjected to the disintegration forces while they are fluidised, that is to say while they are at least partially entrained in drying air or other fluidising gas, and that at least during the time they pass through the sticky stage they should not be allowed to go into a non-fluidised state.

The subjection of the particles to disintegration forces during the fluidised bed drying can be conducted throughout the drying process but it appears that there are no advantages, and there may be some disadvantages, for instance in loss of activity, if the particles are subjected to disintegration forces at near the end of the fluidised bed drying, for instance after they have a dry matter content of about 80-84%. There may be no advantage if they are subjeced to some or all of the disintegration forces too early in the drying stage, and so at least some of the application of disintegration forces is conducted after the particles have a dry matter content of 50%. Thus, the fluidised yeast particles should be subjected to disintegration forces intermittently or, preferably, continuously, throughout at least most of the time that they are in the sticky stage, i.e. a dry matter content of 50 to 70 or 80%.

Expressed another way, it appears desirable that the particles be subjected to disintegration forces at least during the first and/or the second quarters of the total drying time, and conveniently they are subjected to the forces during the third quarter of the drying time as well.

The total drying time depends on the rate, temperature and humidity of the drying air or other gas but is generally $\frac{1}{4}$ to 4 hours, e.g. 1 to $2\frac{1}{2}$ hours. The gas temperature is generally less than 120° C. e.g. 32 to 55° C, the yeast temperature preferably being maintained below 55° C., most preferably below 45° C. The relative humidity of the gas is preferably below 45% at 20° C., especialy below 35%.

In the simplest method the yeast particles are subjected to the forces while they remain in the fluidised bed in which they are being dried. With such an arrangement it is desirable that the disintegration forces be applied for a prolonged period of time, within the relevant periods mentioned above, so as to insure that all yeast particles have the opportunity of being subjected to the forces. However, the yeast particles may be subjected to the disintegration forces outside the fluidised bed. For instance particles may be taken, whilst fluidised, from the bed and passed through suitable disintegration means whilst they are still at least partially entrained in air or other fluidising medium and recycled to the bed, or they may be passed on to a different fluidised bed in which they are further dried.

In one continuous method of drying, moist yeast particles are fed to the first fluidised bed in which they are dried to a predetermined moisture content, are transferred in an entraining gas stream to a second fluidised bed in which they are dried to a further predetermined moisture content and so forth until they have the desired moisture content, and during at least one of the transfer steps they are subjected to the said disintegration forces. Naturally when the yeast particles are subjected to the disintegration forces only for a short time, as when they are taken out of a bed and fed back into it or into another one, it is necessary that they should have a moisture content of between 50 or 60 and 70 or 80% so as to obtain the maximum benefit from the disintegration step.

In view of the known properties of yeast particles as they pass through the sticky stage, it is highly surprising that far from being positively harmful to subject the particles to disintegration forces while they are drying in a fluidised bed drying process, the method of the invention is in fact highly advantageous. It is not at present clear whether the disintegration forces solely act upon aggregates of particles to disintegrate them back into particles of substantially the original particle size or whether they act also upon the original particles in some way as to prevent them aggregating, but probably it is a process of continuous aggregation and disaggregation of small but discrete particles during the sticky stage. Whatever the mechanism, it is possible easily so to choose the disintegration forces as to prevent any substantial increase in particle size during the fluidised bed drying process. Put simply, if the disintegration forces are not great enough, the dried particles will be larger than desired and there will be a substantial increase in average particle size. If the disintegration forces are too great the dried particles will have poor activity, probably because the yeast cells themselves are broken down.

Any means of providing disintegration forces that is capable of providing the very easily obtained balance between excessive and insufficient force can be used. One method of providing the disintegration forces is to subject the particles to the effect of very high gas velocities either in the fluidised bed or in a duct leading out of the fluidized bed and either back into that bed or onto another bed. Such high velocity gas streams may be provided either by directing gas jets into the duct or fluidised bed or by passing a stream of yeast particles entrained in gas through a suitable accelerating device, such as venturi. The disintegration forces may also be provided in the duct or bed by bursting gas bubbles produced by chemical reaction or pressure reduction.

Preferably, however, the disintegration forces are provided by mechanical disintegrating means, although these may in fact bring about disintegration primarily as a result of high gas velocities close to their solid surfaces giving rise to explosive disintegration of aggregates rather than as a result of impact between the solid surfaces and the yeast aggregates. Suitable mechanical disintegration means include one or more members that rotate or oscillate at high speed. It is preferred that during movement the maximum speed is greater than 200, preferably greater than 500, and most preferably greater than 1,000 feet per minute. Speeds of 1,500 to 3,000 feet per minute are often very satisfactory. Sometimes if the speed is considerably higher, for example greater than 5,000 feet per minute and especially if it is greater than 10,000 feet per minute the activity of the yeast may be seriously affected.

Oscillating members such as cutter bars, other bars or sieves may vibrate with such speeds but rotating members, such as blades, rods or discs, are preferred and may rotate at a speed such that at least the outer half of the blade diameter has such a rotational velocity. Normally they rotate at a speed such that the outer peripheral velocity is as indicated above. For instance, a blade or rod, e.g. 2.5 inches in diameter conveniently rotates in the fluidised bed of particles at between 2,000 and 6,000 rpm, most preferably between 3,300 and 5,500 rpm, with best results being obtained at about 4,000 to 5,000 rpm. The free spinning speeds are of course generally higher. Generally any disintegrating means that is a rotating member will rotate at at least 500, and usually at least 1,000 rpm and preferably at the figures given above, and so clearly the invention is providing something more than mere stirring of the bed, e.g. to improve heat transfer.

If the disintegration forces are applied in the fluidised bed they may be provided by a single mechanical disintegrator, in which event it will generally operate over at least a third of the area of the bottom of the bed and be positioned substantially centrally, or they may be provided by a plurality of mechanical disintegrators, together operating over at least a third of the area, some at least of which will generally be positioned around the periphery of the bed. For instance there may be a plurality of rotating blades, rods or discs positioned around the bed. The mechanical disintegrator can be positioned at any height where the yeast is in a fluidised (as defined above) condition, but preferably is close to the base of the bed and is indeed generally in the bottom part of the bed.

Thus it may be in the bottom half of the depth of the bed when fluidised and preferably in the bottom quarter. It is often preferred for it to be less than 2, and most preferably less than 1, e.g. less than 0.5, inches above the base of the bed.

Blades, rods or bars used in a mechanical disintegrator may be of simple rectangular or circular cross-section, but blades may have a pitch, that is to say they should be twisted out of horizontal.

Especially when the disintegrating forces are applied by a central rotor, or by several rotors, it is often desirable to provide in the fluidised bed means for urging particles at the periphery of the bed towards the centre of the bed, so as to counteract any tendency for particles to accumulate at the periphery due to centrifugal action of the one or more rotors. Such means may comprise a member, for instance a rotor blade, that slowly moves around the periphery of the bed forcing the yeast towards the centre of the bed. Thus a preferred apparatus comprises a slowly rotating (e.g. 2 to 50 or 100, preferably 10 to 20, rpm) rotor blade that sweeps the periphery of the bed and one or more fast rotating blades. For instance a single coaxial shaft may drive, at about the same level in the bed, a small diameter disintegrating rotor and a large diameter sweeping blade.

The fluidised bed used in the invention may be of otherwise conventional construction. Thus as shown diagrammatically in the accompanying drawing of an example of such a bed, it will comprise a housing 1 having a perforated base 2 up through which air or other heated fluidising gas can be pumped up from pump 3 and an outlet 4 at the top for the escape of waste gas covered generally by a filter, for example a filter bag 5, to prevent the loss of fine particles with the escaping air. A stirrer rod 6 or other mechanical disintegrating means carried on a rotatable shaft 7 is positioned in the bed 8 of yeast (shown in the fluidised state) at an appropriate height or in a duct leading from that bed. Such apparatus is included within the scope of the invention.

It is preferred that the yeast should contain a wetting agent, for example as described in British Patent Specification No. 1,132,793. Most preferably the yeast contains a mixture of sorbitan fatty acid esters, for example a 1 to 1 mixture of the products known as "Span 40" and "Span 60". The amount of wetting agent is usualy below 3%, for example 0.5 to 2%, based on the dry weight of the yeast. Conveniently it is added either to the yeast cream, to the compressed yeast or to the moist yeast particles.

The following are Examples of the invention.

EXAMPLE 1

This is conducted in a laboratory scale fluidised bed container 6 inches high having an internal diameter at the top of 6 inches and having at the base 1 inch reinforcement ring, giving an internal diameter of 4 inches. Moist yeast particles are produced from compressed yeast treated with 2.75g of a 1 to 1 mixture of Span 40 and Span 60 by a milling method as described in U.S. Pat. No. 1,369,551 and 550 grams of these, having a moisture content of about 32% dry matter, are charged in the fluidised bed dryer. Air having a temperature of 45° C. is pumped up through the bed, sufficient to maintain the fluidised state, for two hours. At the start of the process the outlet air temperature is measured as 20° to 22° C. but is 43° to 44° C. at the end of the process, after two hours. At this time the dry matter content of the the yeast is about 95%. The product is sieved through a sieve having a mesh size of 0.35 mm. The over-sized particles are rejected.

The process is also repeated after fitting in the bottom half of the fluidised bed a four-bladed rotor, each blade being 1.25 inches in length from shaft centre to outer tip of blade and which is driven by a motor above the rotor which is capable of turning the blade at various speeds. The process is also repeated using blades of different pitches.

In each instance the "fermentometer volume" and "A.D.D. bakery proof times" are recorded for the particles that passed through the sieve. It is desirable that the highest fermentometer volume and the lowest A.D.D. time should be obtained. The method of conducting the fermentometer test is as follows:

Weigh out 1.8 grams dried yeast into 100 ml flask containing 40 mls distilled water pre-heated to 38° C. in a water bath. After minutes, swirl yeast suspension to obtain even mixture. Add 20 mls of a solution of salts, consisting of 13.5% NaCl and 1.0% (NH4)SO4. Make up to 100 mls with distilled water. Shake again vigorously, and pipette 15 mls of the yeast suspension into fermetometer jar at 30° C. incubate for 10 minutes and add 20 grams of flour. Stir by hand using a spatula for 40 seconds. Wipe dough off spatula with small piece of tissue, placing tissue into the fermentometer jar. Insert bung tightly. Leave for 13 minutes. Adjust manometer to 0 and close tap. Read after 45 minutes.

The method of measuring the A.D.D. bakery proof time is as follows:

9.5 grams active dried yeast are dry mixed with 1 lb. 4 oz Democrat flour, 10.1 grams salt and 6.0 grams F.A.D. (a proprietary dough additive supplied by The Bristol Arkady Company Limited, Arkady Soya Mills, Old Trafford, Manchester), and allowed to stand for 5 minutes. 350 mls water is added at 88° F and the mixture mixed at that temperature for 4½ minutes in an Artofex mixer. 2 × 16 oz pieces of dough are taken from the mix, are moulded once and placed in 1 lb. bread tins. 7½ minutes after the start of dough mixing the dough subjected to proving at a temperature of 95° F. and relative humidity 85 to 90% and the time recorded to reach a proof height of 10.5 cms.

The conditions used and results obtained are shown in the Table below. From this it is clear that the method of the invention results in a great reduction in oversize, rejected, particles and can be operated in such a way as to result in, at most, only slight reduction in activity of the particles that are small enough to pass through the sieve, although the reduction is greatest at highest blade speeds. In each instance milling started at the beginning of the fluidised bed drying (0minutes) or after 30 or 45 minutes, as shown in the table, and continued to the end of the period shown in the table. BS44 sieve allows only particles smaller than 0.35 mm to pass.

| Start and end of Milling mins. | Blade Pitch mm. | Rotor Blade rpm | Approx. Peripheral Speed of Rotor Blades ft/min | Moisture in yeast % | Passing through BS 44 Sieve % | Fermentometer Vol. (0–45 mins. ml.) | Baker Proof Time Min |
| --- | --- | --- | --- | --- | --- | --- | --- |
| — | — | — | — | 5.8 | 42 | 54 | 35 |
| 0–75 | 3 | 2600 | 1700 | 4.9 | 64 | 54 | 35 |
| 0–90 | 3 | 4400 | 2900 | 5.3 | 88 | 50 | — |
| 0–85 | 3 | 5500 | 3600 | 5.4 | 97 | 44 | — |
| — | — | — | — | 5.7 | 45 | 52 | 35 |
| 0–60 | 5 | 4400 | 2900 | 5.5 | 94 | 51 | — |
| 30–60 | 5 | 4400 | 2900 | 5.9 | 90 | 51 | 36 |
| 45–60 | 5 | 4400 | 2900 | 5.3 | 63 | — | — |
| — | — | — | — | 5.3 | 44 | 54 | 35 |
| 0–80 | 7 | 2600 | 1700 | 5.1 | 74 | 53 | — |
| 0–90 | 7 | 4400 | 2900 | 5.4 | 92 | 49 | — |
| 0–90 | 7 | 5500 | 3600 | 5.6 | 96 | 49 | 41 |

EXAMPLE 2

This is conducted in a fluidised bed container having an internal height of 18 inches and an internal diameter of 30 inches. 90 lbs. of yeast particles as described in Example 1 are charged into the container. Air having a temperature of 48° C. is pumped up through the bed, sufficient to maintain the fluidised state, for 2 hours 20 minutes. At the start of the process the outlet air temperature is 22 to 24° C., but is 44 to 45° C. at the end of the process. At this time the dry matter content of the yeast is 94.1%. The product is sieved through a sieve having a mesh size of 0.35mm, 75% passing through the sieve and remaining particles being rejected. The sieved particles have a fermentometer volume (0 to 45 mins.) of 48 ml and an A.D.D. bakery proof time of 33 mins.

The process is also repeated after fitting in the bottom half of the bed a four bladed rotor each blade being 5 inches in length from the shaft centre to the outer tip of the blade and is driven by a motor above the bed at 500 r.p.m. The dry matter content of the yeast after drying was 94.7 and 88.9% of the yeast passed through the sieve. It had a fermentometer volume (0 to 45 mins) of 53 ml and an A.D.D. bakery proof time of 35 mins.

EXAMPLE 3

The process of Example 1 may be repeated using, instead of the four blade rotor, a single horizontal rod that was rotated about a central vertical shaft at 4400 rpm, giving a peripheral speed of 2900 fpm, with a gap of ¼ to ⅛ inch between it and the base of the bed from the start of drying until the dry matter content was 80 to 85%. If desired a blade profiled to sweep yeast from the outside of the bed to the centre may rotate at 15 rpm on the same shaft as the rod through appropriate gearing.

We claim:

1. A method in which powdered active dried yeast having a dry matter content of 90 to 97% by weight is made by a process comprising drying moist yeast particles less than about 0.35 mm in size in a fluidised bed and subjecting the yeast particles in the fluidised bed to forces capable of disintegrating of yeast particles, said forces being applied continuously through at least most of the time that the dry matter content is between 50 and 70% and said forces being sufficient to prevent any substantial increase in particle size but insufficient to break the yeast cells themselves, with the resulting dried yeast particles substantially all passing through a sieve having a mesh size of 0.35 mm.

2. A method according to claim 1, in which the disintegration forces are provided by mechanical disintegration means comprising one or more members that rotate at 2000 to 6000 rpm.

3. A method according to claim 2, in which said member or members rotate at 4000 to 5000 rpm.

4. A method according to claim 2, in which the said member or members together operate over at least a third of the area of the bed.

5. A method according to claim 2, in which the said member or members are in the bottom half of the bed of yeast particles when fluidised.

6. A method according to claim 1, in which the disintegration forces are applied continuously in the fluidised bed in which the yeast is being dried during at least the first and/or second quarters of the total drying time.

7. A method according to claim 1 in which the yeast has a dry matter content initially of 27 to 40% and finally of 90 to 97%, and the fluidised bed drying is conducted for ¼ to 4 hours.

* * * * *